United States Patent
Bachert et al.

(10) Patent No.: US 10,195,305 B2
(45) Date of Patent: Feb. 5, 2019

(54) BIOACTIVE FLOWABLE WASH-OUT RESISTANT BONE GRAFT MATERIAL AND METHOD FOR PRODUCTION THEREOF

(71) Applicant: Orthovita, Inc., Malvern, PA (US)

(72) Inventors: Alice Bachert, Havertown, PA (US); Jeremy Mercuri, Piedmont, SC (US)

(73) Assignee: Orthovita, Inc., Malvern, PA (US)

( * ) Notice: Subject to any disclaimer, the term of this patent is extended or adjusted under 35 U.S.C. 154(b) by 802 days.

(21) Appl. No.: 14/666,985

(22) Filed: Mar. 24, 2015

(65) Prior Publication Data
US 2016/0279287 A1  Sep. 29, 2016

(51) Int. Cl.
| | | |
|---|---|---|
| A61B 17/58 | (2006.01) |
| A61L 27/10 | (2006.01) |
| A61L 27/46 | (2006.01) |
| A61L 27/52 | (2006.01) |
| A61L 27/56 | (2006.01) |
| A61L 27/58 | (2006.01) |
| A61L 24/00 | (2006.01) |
| A61B 17/88 | (2006.01) |
| A61L 27/12 | (2006.01) |

(Continued)

(52) U.S. Cl.
CPC .......... *A61L 27/10* (2013.01); *A61B 17/8822* (2013.01); *A61L 24/0031* (2013.01); *A61L 24/0036* (2013.01); *A61L 24/0042* (2013.01); *A61L 24/0094* (2013.01); *A61L 27/12* (2013.01); *A61L 27/20* (2013.01); *A61L 27/26* (2013.01); *A61L 27/46* (2013.01); *A61L 27/52* (2013.01); *A61L 27/54* (2013.01); *A61L 27/56* (2013.01); *A61L 27/58* (2013.01); *A61L 2300/112* (2013.01); *A61L 2400/06* (2013.01); *A61L 2430/02* (2013.01)

(58) Field of Classification Search
CPC ............ A61B 17/8825; A61B 17/8802; A61B 17/3472; A61B 17/7097; A61B 17/8822; A61B 17/70; A61B 2/4601; A61B 2002/2835

See application file for complete search history.

(56) References Cited

U.S. PATENT DOCUMENTS

| | | | |
|---|---|---|---|
| 4,795,467 A | 1/1989 | Piez et al. |
| 5,053,212 A | 10/1991 | Constantz et al. |

(Continued)

FOREIGN PATENT DOCUMENTS

| | | |
|---|---|---|
| WO | 2007068489 A2 | 6/2007 |
| WO | 2008032054 A2 | 3/2008 |
| WO | 2011053725 A1 | 5/2011 |

OTHER PUBLICATIONS

Goasin, A. Bioactive Glass for Bone Replacement in Craniomaxillofacial Reconstruction, Plastic and Reconstructive Surgery (2004) vol. 114, No. 2, pp. 590-593.

(Continued)

*Primary Examiner* — Eduardo C Robert
*Assistant Examiner* — Tara R Carter
(74) *Attorney, Agent, or Firm* — Lerner, David, Littenberg, Krumholz & Mentlik, LLP

(57) ABSTRACT

The present invention relates to a flowable bone graft material including an inorganic composition comprising calcium phosphate having a particle size of about 100 μm to about 1,000 μm, bioactive glass, and one or more biocompatible polymers comprising carboxymethyl cellulose and a fluid.

12 Claims, 8 Drawing Sheets

(51) Int. Cl.
*A61L 27/20* (2006.01)
*A61L 27/26* (2006.01)
*A61L 27/54* (2006.01)

(56) References Cited

U.S. PATENT DOCUMENTS

| | | | |
|---|---|---|---|
| 5,324,519 A | 6/1994 | Dunn et al. | |
| 5,352,715 A | 10/1994 | Wallace et al. | |
| 5,429,996 A | 7/1995 | Kaneko | |
| 5,591,453 A | 1/1997 | Ducheyne et al. | |
| 5,597,897 A * | 1/1997 | Ron | A61K 9/0024 530/350 |
| 5,643,789 A | 7/1997 | Ducheyne et al. | |
| 5,648,301 A | 7/1997 | Ducheyne et al. | |
| 5,676,720 A | 10/1997 | Ducheyne et al. | |
| 5,811,302 A | 9/1998 | Ducheyne et al. | |
| 5,817,327 A | 10/1998 | Ducheyne et al. | |
| 5,849,331 A | 12/1998 | Ducheyne et al. | |
| 5,861,176 A | 1/1999 | Ducheyne et al. | |
| 5,871,777 A | 2/1999 | Ducheyne et al. | |
| 5,874,109 A | 2/1999 | Ducheyne et al. | |
| 5,914,356 A | 6/1999 | Erbe | |
| 5,939,039 A | 8/1999 | Sapieszko et al. | |
| 5,964,807 A | 10/1999 | Gan et al. | |
| 6,214,368 B1 | 4/2001 | Lee et al. | |
| 6,287,341 B1 | 9/2001 | Lee et al. | |
| 6,288,043 B1 | 9/2001 | Spiro et al. | |
| 6,383,519 B1 | 5/2002 | Sapieszko et al. | |
| 6,413,538 B1 | 7/2002 | Garcia et al. | |
| 6,458,162 B1 | 10/2002 | Koblish et al. | |
| 6,482,444 B1 | 11/2002 | Bellantone et al. | |
| 6,521,246 B2 | 2/2003 | Sapieszko et al. | |
| 6,537,574 B1 | 3/2003 | Hubbard | |
| 6,630,153 B2 | 10/2003 | Long et al. | |
| 6,652,887 B1 | 11/2003 | Richelsoph et al. | |
| 6,692,760 B2 | 2/2004 | Miyamoto et al. | |
| 6,709,744 B1 | 3/2004 | Day et al. | |
| 6,736,799 B1 | 5/2004 | Erbe et al. | |
| 6,756,060 B1 | 6/2004 | Greenspan et al. | |
| 6,863,899 B2 | 3/2005 | Koblish et al. | |
| 6,991,803 B2 | 1/2006 | Sapieszko et al. | |
| 7,052,517 B2 | 5/2006 | Murphy et al. | |
| 7,189,263 B2 | 3/2007 | Erbe et al. | |
| 7,189,409 B2 | 3/2007 | Pirhonen et al. | |
| 7,531,004 B2 | 5/2009 | Bagga et al. | |
| 7,534,451 B2 | 5/2009 | Erbe et al. | |
| 7,709,081 B2 | 5/2010 | Zenati et al. | |
| 8,287,915 B2 | 10/2012 | Clineff et al. | |
| 8,303,967 B2 | 11/2012 | Clineff et al. | |
| 8,475,824 B2 | 7/2013 | McKay | |
| 8,580,865 B2 | 11/2013 | Peters et al. | |
| 2002/0127720 A1 | 9/2002 | Erbe et al. | |
| 2005/0288795 A1 | 12/2005 | Bagga et al. | |
| 2007/0122447 A1* | 5/2007 | Koblish | A61B 17/866 424/423 |
| 2007/0128245 A1* | 6/2007 | Rosenberg | A61K 9/0024 424/423 |
| 2007/0286884 A1* | 12/2007 | Serafica | A61L 27/20 424/423 |
| 2008/0187571 A1* | 8/2008 | Clineff | A61L 27/10 424/426 |
| 2012/0022542 A1* | 1/2012 | Boger | A61L 27/46 606/94 |
| 2012/0141595 A1* | 6/2012 | Tseng | A61K 35/44 424/583 |
| 2014/0271779 A1 | 9/2014 | Bagga et al. | |

OTHER PUBLICATIONS

Kingery, W.D., Introduction of Ceramics, Wiley Series on the Science and Technology of Materials, 1st ed., Hollowman, J.H., et al. (Eds.), Wiley & Sons, 1960, p. 409-417.

Extended European Search Report in European Patent Application No. 16161967, dated Aug. 4, 2016, 2 pages.

* cited by examiner

BIOACTIVE FLOWABLE WASH-OUT RESISTANT BONE GRAFT MATERIAL AND METHOD FOR PRODUCTION THEREOF

BACKGROUND OF THE INVENTION

The use of natural and synthetic materials for bone repair is known. Most of the synthetic materials share numerous advantages over natural materials (including allograft bone, autograft bone and demineralized bone matrix ("DBM")) such as unlimited supply, elimination of disease transmission, elimination of second surgery, and the ability to be shaped into various shapes and sizes. Many synthetic bone grafts include materials that closely mimic mammalian bone, such as compositions containing calcium phosphates. Exemplary calcium phosphate compositions contain type-B carbonated hydroxyapatite $[Ca_5(PO_4)_{3x}(CO_3)x(OH)]$, which is the principal mineral phase found in the mammalian body. The ultimate composition, crystal size, morphology, and structure of the body portions formed from the hydroxyapatite are determined by variations in the protein and organic content. Calcium phosphate ceramics have been fabricated and implanted in mammals in various forms including, but not limited to, shaped bodies and cements. Different stoichiometric compositions such as hydroxyapatite ("HAp"), tricalcium phosphate ("TCP"), tetracalcium phosphate ("TTCP"), and other calcium phosphate salts and minerals, have all been employed to match the adaptability, biocompatibility, structure, and strength of natural bone. The role of pore size and porosity in promoting revascularization, healing, and remodeling of bone has been recognized as a critical property for bone grafting materials. The preparation of exemplary porous calcium phosphate materials that closely resemble bone have been disclosed, for instance, in U.S. Pat. Nos. 6,383,519; 6,521,246 and 6,991,803 incorporated herein by reference in their entirety.

Recently, in an attempt to broaden the use of bone graft materials throughout the body, pliable and injectable bone graft compositions have been fabricated. Some of these attempts have been disclosed in U.S. Pat. No. 5,324,519 to Dunn, et al.; U.S. Pat. No. 5,352,715 to Wallace et al.; U.S. Pat. No. 6,287,341 to Lee et al.; U.S. Pat. No. 6,214,368 to Lee et al.; U.S. Pat. No. 6,652,887 to Richelsoph et al.; and U.S. Pat. No. 6,288,043 to Spiro et al. However, these attempts suffer from numerous shortcomings. Some compositions are made of thermoplastic polymers as opposed to calcium phosphate. There are injectable implant compositions that teach having ceramic:collagen ratios requiring a collagen dominance. There are also compositions used as implants made of poorly crystalline apatitic calcium phosphate defined by a specific XRD spectrum and FTIR pattern. Other attempts have focused on compositions made from calcium sulfate.

Furthermore, many of these bone attempts include materials that do not optimally resorb (e.g., thermoplastic polymers, amorphous calcium phosphate, calcium sulfate dihydrate) or structures that do not have the ideal porosity and pore size distribution to promote bone formation. Other attempts require the addition of a carrier, such as hyaluronic acid or glycerol, or a plasticizer in a high percentage so that the compositions may be shaped or injected. Several also require that the mineral component particle size be smaller than 250 μm to facilitate injection.

In addition, because the flowability and wash-out resistant properties have an inverse relationship, there exists a problem that if the flowability/injectability of the bone graft material increases, the wash-out resistant property thereof decreases.

Therefore, there is a need for injectable, resorbable bone graft materials with improved handling properties that maintain physical integrity in a wet environment, such as in the presence of body fluids at a defect site.

There is also a need for resorbable, porous, injectable bone graft materials that maintain ideal osteoconductivity properties, offer convenient delivery for a variety of applications and can occupy voids of varying shapes for restoring defects in bone.

BRIEF SUMMARY OF THE INVENTION

Described herein are flowable bone graft materials with improved osteoconductive properties that also exhibit improved wash-out resistant and therefore can maintain physical integrity in a wet environment.

In one embodiment, the flowable bone graft material contains an inorganic composition comprising calcium phosphate having a particle size of about 100 μm to about 1,000 μm, bioactive glass, and one or more biocompatible polymers, and a fluid.

In one embodiment, the biocompatible polymer may be carboxymethyl cellulose and gelatin. The carboxymethyl cellulose may have molecular weight of about 100,000 Mw to about 300,000 Mw. In another embodiment, the viscosity of the carboxymethyl cellulose may be from about 400 MPa-s to about 800 MPa-s. In yet another embodiment, degree of substitution of the carboxymethyl celullose may be from about 0.6 to about 0.8, and preferably about 0.7. An example of the preferred biocompatible polymer is sodium carboxymethyl cellulose.

Kits providing an easy-to-use dose of the bone graft material are also contemplated. In one embodiment, a kit comprises a syringe containing a dry bone graft material containing calcium phosphate having a particle size of about 100 μm to about 1,000 μm, bioactive glass, and one or more biocompatible polymers containing carboxymethyl cellulose. In another embodiment, the syringe further contains gelatin as an additional biocompatible polymer. In yet another embodiment, the syringe does not contain any fluid such as bone marrow aspirate, blood or saline.

In one embodiment, the kit furtherber comprises a hydration syringe to be filled with a fluid, such as bone marrow aspirate, blood or saline, a vacuum syringe to pull vacuum and expel air in the syringe containing the dry bone graft material, and a cannula for injecting the bone graft material once the dry bone graft material and the fluid are mixed.

Various methods for manufacturing the bone graft materials are also contemplated. In one embodiment, a method for repairing bone in an animal comprises forming a flowable bone graft material comprising an inorganic composition comprising calcium phosphate having a particle size of about 100 μm to about 1,000 μm, bioactive glass, and one or more biocompatible polymers, and a fluid; accessing a site to be restored; and delivering the flowable bone graft material to the site. In another embodiment, the bone graft material contains gelatin as an additional biocompatible polymer.

DETAILED DESCRIPTION

Figure 1:
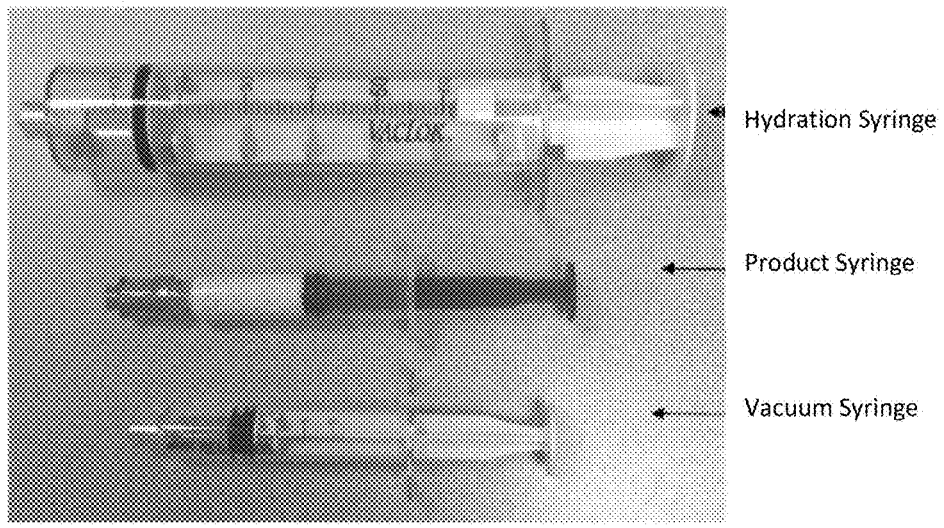
FIG. 1 depicts an embodiment of a kit described herein including a syringe (product syringe), a hydration syringe and a vacuum syringe. The dry bone graft material in accordance with the present invention is housed in a syringe (product syringe) containing an inorganic composition comprising calcium phosphate having a particle size of about 100 μm to about 1,000 μm, bioactive glass, sodium carboxymethyl cellulose, and gelatin, without any fluid.

The invention will be described in more detail below.

While the specification concludes with the claims particularly pointing out and distinctly claiming the invention, it is believed that the invention described herein will be better understood from the following description. All temperatures are in degrees Celsius unless specified otherwise. The invention described herein can comprise (open ended) or consist essentially of the components of the invention described herein as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

It should be further understood that a description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

The term "bone graft material" herein is used interchangeably with "bone graft" and "implant".

The term "morsel" used herein is used interchangeably with "particle".

The term "flowable" herein is used interchangeably with injectable. The term "flowable" as used in accordance with the present invention herein means that when the dry bone graft material is mixed with a fluid, the bone graft material may be delivered to the site of application using a cannula, a needle, a catheter, a syringe or a specially designed mixing device by the action of an applied injection force. This injection force is tested at an ambient temperature from 18° C. to 22° C. as set out in Experimental Example 3 below, and does not exceed 140 N, preferably 120 N, more preferably 100 N to allow ease of the injectability for the end user.

The term "biocompatible" used in conjunction with a bone graft material or any components thereof, for example, a biocompatible polymer, contemplates that the bone graft material or any components of bone graft material that is not rejected by soft tissue or hard tissue when used in vivo in the intended application.

The term "fluid" used herein means any liquid which may be mixed with dry bone graft materials to form a flowable bone graft material. Examples of such fluid include, without any limitation, a bone marrow aspirate, blood, saline, antibiotics and proteins such as bone morphogenetic proteins (BMPs) and the like.

It has been discovered that admixing porous inorganic composition and bioactive glass with one or more biocompatible polymers comprising carboxymethyl cellulose greatly improves flowability while maintaining physical integrity in a wet environment such as in the presence of body fluids. The dry bone graft material comprising the porous inorganic composition, bioactive glass and one or more biocompatible polymers becomes pliable after contact with a fluid and can be delivered via injection through a syringe or a delivery tube of varying diameters, particularly of small diameters, while maintaining optimal characteristics for resorption, cellular infiltration and imbibation. Kits containing easy-to-use doses of dry bone graft materials are significant advancement over current bone graft systems for clinical applications as the bone graft materials described herein is flowable but yet also has improved wash-out resistant properties and therefore can maintain physical integrity in a wet environment. Flowable bone graft materials described herein may be flexible or moldable, and more preferably injectable for use in MIS procedures. The nature of the biocompatible polymer(s) included in the bone graft materials affect the flowability, flexibility, or moldability of the graft material, while maintaining integrity in a wet environment.

Porous Inorganic Composition

A porous inorganic composition in the bone graft materials described herein includes calcium phosphates. Various calcium phosphates are contemplated and include, for example, tricalcium phosphate, β-tricalcium phosphate (β-TCP), α-tricalcium phosphate (α-TCP), and apatites such as hydroxyapatite. However, for the sake of brevity, "calcium phosphate" includes any calcium salt known to those skilled in the art. The preparation of various forms of calcium phosphate for use in the present invention is described in U.S. Pat. Nos. 5,939,039, 6,383,519, 6,521,246, and 6,991,803, assigned to the assignee of the present invention and incorporated herein by references in their entireties. An exemplary calcium phosphate product is Vitoss® Bone Graft Substitute (Orthovita, Inc., Malvern, Pa.).

In accordance with the present invention, some bone graft materials disclosed may partially comprise materials, or morsels, resulting from an oxidation-reduction reaction. These materials may be produced by methods comprising preparing an aqueous solution of a metal cation and at least one oxidizing agent. The solution is augmented with at least one soluble precursor anion oxidizable by said oxidizing agent to give rise to the precipitant oxoanion. The oxidation-reduction reaction thus contemplated is conveniently initiated by heating the solution under conditions of temperature and pressure effective to give rise to said reaction. In accordance with preferred embodiments of the invention, the oxidation-reduction reaction causes at least one gaseous product to evolve and the desired intermediate precursor mineral to precipitate from the solution. In accordance with certain preferred embodiments of the present invention, a reactive blend in accordance with the invention may be imbibed into a material that is capable of absorbing it to produce a porous mineral. It may be preferred that the material have significant porosity, be capable of absorbing significant amounts of the reactive blend via capillary action, and that the same be substantially inert to reaction with the blend prior to its autologous oxidation-reduction reaction.

The intermediate precursor mineral thus prepared can either be used "as is" or can be treated in a number of ways. Thus, it may be heat-treated greater than about 800° C. or, preferably, greater than about 1100° C. in accordance with one or more paradigms to give rise to a preselected crystal structure or other preselected morphological structures therein. In accordance with preferred embodiments, the oxidizing agent is nitrate ion and the gaseous product is a nitrogen oxide, generically depicted as $NO_x(g)$. It is preferred that the precursor mineral provided by the present methods be substantially homogeneous. As used in this context, substantially homogenous means that the porosity and pore size distribution throughout the precursor mineral is the same throughout.

In accordance with other preferred embodiments, the intermediate precursor mineral provided by the present invention may be any calcium salt. Subsequent modest heat treatments convert the intermediate material to, e.g., novel monophasic calcium phosphate minerals or novel biphasic β-tricalcium phosphate (β-TCP)+type-B, carbonated apatite (c-HAp) $[β-Ca_3(PO_4)_2+Ca_5(PO_4)_{3-x}(CO_3)x(OH)]$ particulates. More preferably, the heat treatment converts the intermediate material to a predominantly β-TCP material.

In one embodiment, the calcium phosphate is β-TCP. In preferred embodiments, the calcium phosphate is porous. In another embodiment, the calcium phosphate contains micro-, meso-, and macroporosity. In yet another embodiment, the porosity of the calcium phosphate is interconnected. Macroporosity is characterized by pore diameters greater than about 100 μm and, in some embodiments, up to about 1000 μm to 2000 μm. Mesoporosity is characterized by pore diameters between about 10 μm and 100 μm, while microporosity occurs when pores have diameters below about 10 μm. It is preferred that macro-, meso-, and microporosity occur simultaneously and are interconnected in products of the invention. It is not necessary to quantify each type of porosity to a high degree. Rather, persons skilled in the art can easily determine whether a material has each type of porosity through examination, such as through the preferred methods of mercury intrusion porosimetry, helium pycnometry or scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso-, and microporosity.

In one embodiment, the calcium phosphate is in the form of particles or morsels and may contain a porous structure as described herein.

It will be appreciated that in some embodiments of materials prepared in accordance with this invention the overall porosity will be high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with Kingery, W. D., Introduction to Ceramics, Wiley Series on the Science and Technology of Materials, $1^{st}$ Ed., Hollowman, J. H., et al. (Eds.), Wiley & Sons, 1960, p. 409-417, which provides a formula for determination of porosity. Expressing porosity as a percentage yields pore volume. The formula is: Pore Volume=$(1-f_p)$ 100%, where $f_p$ is fraction of theoretical density achieved.

Porosity can be measured by Helium Pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume-measured volume)/apparent volume. Porosity and pore size distribution may also be measured by mercury intrusion porosimetry.

Pore volumes in excess of about 30% may be achieved in accordance with some embodiments of the porous inorganic composition while materials having pore volumes in excess of 50% or 60% may also be routinely attainable. Some embodiments of the invention may have pore volumes of at least about 70%. Some embodiments that may be preferred have pore volumes in excess of about 75%, with 80% being still more preferred. Some embodiments may have pore volume greater than about 90%, more preferably greater than about 92%. In some preferred cases, such high pore volumes are attained while also attaining the presence of macro- meso- and microporosity as well as physical stability of the materials produced.

It will be appreciated that the morsel size will be selected considering the desired delivery apparatus. For example, for delivery of a flowable composition using a standard syringe, it will be necessary to select a morsel size that fits through the syringe orifice. One preferred size range for the morsels of the present invention is from about 100 µm to 1,000 µm, preferably from about 200 µm to 900 µm, and more preferably from about 212 µm to about 850 µm. Unless otherwise specified, morsel size as used herein refers to the sieve size used to partition the calcium phosphate morsels.

Due to the high porosity and broad pore size distribution (1 µm to 1000 µm) of the bone graft materials, the implant is not only able to wick/soak/imbibe materials very quickly, but is also capable of retaining them. A variety of fluids could be used with the present invention including blood, bone marrow aspirate, saline, antibiotics and proteins such as bone morphogenetic proteins (BMPs). Materials of the present invention can also be imbibed with cells (e.g., fibroblasts, mesenchymal, stromal, marrow and stem cells), platelet rich plasma, other biological fluids, and any combination of the above. Bone grafts of the present invention actually hold, maintain, and/or retain fluids once they are imbibed, allowing for contained, localized delivery of imbibed fluids. This capability has utility in cell-seeding, drug delivery, and delivery of biologic molecules as well as in the application of bone tissue engineering, orthopaedics, and carriers of pharmaceuticals.

Biocompatible Polymer(s)

The inclusion of the one or more biocompatible polymers in the bone graft material described herein lends improved handling and flowability, as well as the ability to maintain integrity in a wet environment.

Any suitable resorbable biocompatible polymer may be used in accordance with the present invention. In a preferred embodiment, the biocompatible polymer may be lower alkyl cellulose ethers. Examples of a lower alkyl cellulose ethers include, without limitation, methylcellulose, sodium carboxymethyl cellulose, hydroxyethyl cellulose, hydroxypropyl cellulose, hydroxypropylmethylcellulose, carboxymethyl cellulose, and mixtures thereof. In one embodiment, the molecular weight of lower alkyl cellulose ethers is from about 49,000 Mw to about 725,000 Mw, and preferably from about 100,000 Mw to about 300,000 Mw, and more preferably from about 220,000 MW to about 270,000 Mw. With respect to the amount of the lower alkyl cellulose ethers, it is present in an amount ranging from about 3% w/w to about 20% w/w, preferably from about 5% w/w to about 15% w/w, and more preferably from about 8% w/w to about 10% w/w based on the total weight of the flowable bone graft material. In a preferred embodiment, viscosity of the lower alkyl cellulose ethers is from about 100 MPa-s to about 1000 MPa-s, and preferably from about 300 MPa-s to about 800 MPa-s, and more preferably from about 400 MPa-s to about 800 MPa-s, and the degree of substitution of the lower alkyl cellulose ethers is from about 0.6 to about 1.2, and more preferably about 0.6 to 0.8, more preferably, is about 0.7.

In one embodiment, the lower alkyl cellulose ethers is sodium carboxymethyl cellulose. In yet another embodiment, the molecular weight of sodium carboxymethyl cellulose is from about 49,000 Mw to about 725,000 Mw, preferably from about 100,000 Mw to about 300,000 Mw, and more preferably from about 220,000 MW to about 270,000 Mw. Due to sodium carboxymethyl cellulose's high molecular weight, it is believed that the sodium carboxymethyl cellulose acts as a binding agent that physically blends with and entangles the components of the dry bone graft material. Furthermore, it is believed that sodium carboxymethyl cellulose's hydrophilicity may aid in preventing disintegration of the dry bone graft material by sequestering water molecules and thus minimizing their interaction with the other components of the formulation. It is also plausible that the anionic nature of sodium carboxymethyl cellulose may contribute to establishing bonding forces with the calcium component of the calcium phosphate, such as β-tricalcium phosphate.

In a preferred embodiment, viscosity of sodium carboxymethyl cellulose is from about 100 MPa-s to about 1000 MPa-s, preferably from about 300 MPa-s to about 800 MPa-s and more preferably from about 400 MPa-s to about 800 MPa-s, and the degree of substitution of sodium carboxymethyl cellulose is from about 0.6 to about 1.2, and more preferably about 0.6 to 0.8, more preferably, is about 0.7.

With respect to the amount of the sodium carboxymethyl cellulose, preferably, it is present in an amount from about 5% w/w to about 15% w/w, preferably from about 8% to about 12%, and more preferably from about 9% w/w to about 10% w/w based on the total weight of the flowable bone graft material.

In other embodiments, the biocompatible polymer may further contain gelatin and other suitable polymers described, for example, in U.S. Pat. Nos. 7,189,263; 7,534,451; 7,531,004; and 8,287915, assigned to the assignee of the present invention and incorporated herein by references in their entireties. Examples of other suitable polymer include, without limitation, polycaprolactones (PCL), polyglycolic acid (PGA), poly-L-Lactic acid (PL-LA), polysulfones, polyolefins, polyvinyl alcohol (PVA), polyalkenoics, polyacrylic acids (PAA), polyesters and mixtures thereof.

Some embodiments of the present invention further contain collagen that comprises up to 100% Type I collagen. In other embodiments, the collagens used may be predominantly, or up to about 90%, of Type I collagen with up to about 5% of Type III collagen or up to about 5% of other types of collagen. Suitable Type I collagens include native fibrous insoluble human, bovine, porcine, or synthetic collagen, soluble collagen, reconstituted collagen, or combinations thereof. Some embodiments of the present invention do not contain collagen.

The flowable bone graft material contains one or more biocompatible polymers including lower alkyl cellulose ethers, such as sodium carboxymethyl cellulose. In another embodiment, the flowable bone graft material contains at least two biocompatible polymers. In a preferred embodiment, the flowable bone graft material contains carboxymethyl cellulose and gelatin without collagen. In a more preferred embodiment, the flowable bone graft material contains sodium carboxymethyl cellulose and gelatin without collagen. In another preferred embodiment, the flowable bone graft material contains gelatin and at least one lower alkyl cellulose ether without collagen. In another preferred embodiment, the flowable bone graft material contains gelatin, collagen and at least one lower alkyl ether of cellulose.

Bioactive Glass/Glass-Ceramic

"Bioactive glass" as used herein may be any alkali-containing ceramic, glass, glass-ceramic, or crystalline material that reacts as it comes in contact with physiologic fluids including, but not limited to, blood and serum, which leads to bone formation. In preferred embodiments, bioactive glasses, when placed in physiologic fluids, form an apatite layer on their surface. Examples of preferred bioactive glasses suitable for use in the present invention are described in U.S. Pat. No. 5,914,356, incorporated herein by reference. Suitable bioactive materials also include 45S5 glass and glass-ceramic, 58S5 glass, S53P4 glass, apatite-wollastonite containing glass and glass-ceramic. Preferably, the bioactive glass is a glass-ceramic composition comprising heterogeneous particles having an irregular morphology and regions of combeite crystallites ("Combeite glass-ceramic" having the chemical composition $Na_4Ca_3Si_6O_{16}(OH)_2$). In some embodiments, the bioactive glass comprises about 5-50% by volume of regions of combeite crystallites. Preferred bioactive glasses suitable for use in the present invention are those compositions comprising calcium-phosphorous-sodium-silicate and calcium-phosphorous-silicate. Such bioactive glasses include NovaBone and NovaBone-AR, distributed by NovaBone Products, LLC, Alachua, Fla. Further bioactive glass compositions that may be suitable for use in the present invention are described in U.S. Pat. No. 6,709,744.

While not wishing to be bound by theory, it is believed that resorption of bioactive glass particles of about 150 µm or less occurs as silica as released within the apatite gel layer, while larger particles are eventually broken down by osteoclasts (Goasin, A. Bioactive Glass for Bone Replacement in Craniomaxillofacial Reconstruction, Plastic and Reconstructive Surgery (2004) Vol. 114, No. 2, pp. 590-593). It is presently believed that the bone graft materials of the present invention provide an appropriate scaffold for bone growth independent of the bioactive glass. Again, while not wishing to be bound by theory, the role of the bioactive glass in bone graft materials described herein is believed to be stimulatory to osteoblasts, and as such, large particles of glass (>150 µm) which may also provide a scaffold for bone growth are not necessary, and thus the particles which are resorbed via dissolution are preferred. However, all sizes of resorbable glass particles are contemplated as suitable.

Particle size measurement is well known in the art. Unless otherwise specified, particle size as used herein refers to the sieve size used to partition the glass particles. The bioactive glass particles used in accordance with the present invention are preferably about 20 µm to about 200 µm. The bioactive glass particles may be on the order of about 100 µm or less, on the order of about 150 µm or less, or the bioactive glass particles can be on the order of about 30 µm to about 200 µm, The bioactive glass particles may be bimodal in nature, with distinct particles in the size range 32 µm-90 µm and particles in the size range 90 µm-150 µm. The bioactive glass particles may be solid or may even be porous. In a preferred embodiment, the bioactive glass is nonporous.

The biocompatible polymer and bioactive glass may be combined with the porous inorganic composition comprising calcium phosphate by blending to form a substantially homogenous mixture. As used in this context, "substantially homogenous" means that the ratio of components within the mixture is the same throughout. The porous inorganic composition comprising calcium phosphate calcium phosphate, biocompatible polymer, and bioactive glass may also be combined to form a composite matrix in various shapes and sizes.

In one method, the three constituents (the porous inorganic composition, biocompatible polymer, and bioactive glass), are mixed while the pH of the homogenate is monitored. The bioactive glass component is sensitive to aqueous environments, so monitoring the pH of the homogenate ensures that the bioactive glass component in the mix is not altered via premature leaching of ions that are necessary for promoting osteoactivity. The homogenate is then dispersed into defined molds, freeze-dried, and for some embodiments, crosslinked.

In certain embodiments, the bioactive glass could be in the form of a coating on the biocompatible polymer strands. In others, the bioactive glass could be in the form of a coating on the biocompatible polymer(s) and calcium phosphate homogenous mixture. Upon treatment using various preferred heating, freeze-drying, and crosslinking techniques, such mixtures may form the bone graft materials.

Flowable Bone Graft Material

The admixture of the one or more biocompatible polymers and bioactive glass with the highly porous calcium phosphate results in a graft material that is highly porous with a broad pore size distribution, and increased handling properties beyond that which is achievable with some forms of calcium phosphate alone.

One unique feature of the flowable bone graft materials of the present invention is that it can be used in MIS (minimally invasive spine surgery procedures) as it is resistant to wash-out from the site. Another unique feature of the flowable bone graft of the present invention is that it is capable of maintaining injectability without separation of the fluid from dry bone graft material having the porous inorganic composition, one or more biocompatible polymers and bioactive glass, or separation of the components of the dry bone graft material from each other.

Moreover, bone graft materials of the present invention exhibit improved osteoconductive and osteostimulatory properties over previous bone grafts. The resorption profile of some of the embodiments of the present invention may vary depending upon the amount, nature, and source of the biocompatible polymer used. One reason that may explain the superior resorption properties of the present invention is the high degree of porosity retained even upon admixing the biocompatible polymer and bioactive glass to form the reaction product.

Flowable bone grafts of the present invention are highly porous, highly porous being defined as having a total porosity of greater than about 30%, preferably greater than about 50% and less than about 100%.

The final prepared volume of flowable graft materials of the present invention are based on the weight of the dry bone graft material and reconstitution/hydration volume of a fluid. Fluids that may be used in the present invention may be bone marrow aspirate, blood, saline, antibiotics and proteins such as bone morphogenetic proteins (BMPs) and the like. For example, in one embodiment, 0.8 g of dry bone graft material is reconstituted/hydrated with 1.6 cc of saline to form a flowable bone graft material in accordance with the present invention. In some embodiments, the reconstitution/hydration ratio (weight of dry bone graft material:hydration volume) is from 1:1.2 to 1:3, preferably 1:1.38 to 1:1.25; more preferably from 1:1.8 to 1.25, and most preferably 1:2.

If the hydration is less than 1:1.2, the injection forced needed to deliver the final prepared volume of flowable graft material to the site of the application using a cannula, a needle, a catheter, a syringe or a specially designed mixing device may exceed 100 N and therefore does not to allow ease of the injectability for the end user.

If the hydration is more than 1:3, there may be a separation of the fluid from dry bone graft material and the wash-out resistance of the final flowable bone graft material may be deteriorated.

Due to the high porosity and broad pore size distribution (1 µm-1000 µm) of one of the component of the bone graft material, i.e., inorganic composition including calcium phosphate, the implant is not only able to wick/soak/imbibe materials very quickly, but is also capable of retaining them. Materials of the present invention can also be imbibed with cells (e.g., bone cells such as osteoblasts and osteocytes, fibroblasts, mesenchymal, stromal, marrow and stem cells), platelet rich plasma, other biological fluids, and any combination of the above.

Bone grafts of the present invention actually hold, maintain, and/or retain fluids once they are imbibed or in contact with fluid, allowing for contained, localized delivery of imbibed fluids. This capability has utility in cell-seeding, drug delivery, and delivery of biologic molecules as well as in the application of bone tissue engineering, orthopaedics, and carriers of pharmaceuticals. The cells may be seeded onto the graft prior to implantation. Similarly, molecules or proteins could be soaked into the graft prior to implantation. If desired, the present invention can be mixed with other available bone graft materials including autograft and allograft bone chips, demineralized bone matrix (DBM) and synthetic morsels.

In some embodiments, the dry bone graft material of the present invention comprises from about 40% to about 80%, preferably about 50% to about 70%, more preferably 55% to 65% by weight of calcium phosphate; about 10% to about 50%, preferably about 15% to about 40%, more preferably 15% to about 35% by weight of biocompatible polymer; and about 5% to about 25%, preferably about 10-20%, more preferably from about 10% to about 15% by weight of bioactive glass, relative to the total weight of the dry bone graft materials.

In certain embodiments, dry bone graft materials of the present invention comprise calcium phosphate, polymer and bioactive glass in a weight ratio of 50:30:20 to 70:20:5, preferably from 55:28:15 to 65.5:22:10, and more preferably from 62.5:22.5:15 to 62.5:25:12.5. The mass ratios may be altered without unreasonable testing using methods readily available in the art while still maintaining all the properties (e.g., porosity, pore size distribution) that attribute to an effective flowable bone graft (e.g., simultaneous bone formation, wash-out resistance, strength and graft resorption).

Preferably, dry bone graft materials of the present invention may comprise up to about 70% by weight of calcium phosphate. In certain embodiments, bone graft materials of the present invention may comprise up to about 65% by weight of calcium phosphate. The bone graft materials of the present invention may also comprise up to about 60% by weight of calcium phosphate.

Preferably, the bone graft materials may comprise up to about 40% by weight of polymer. In certain other variants of the present invention, the bone graft materials may comprise up to about 30% by weight of polymer. In others, the bone graft materials may comprise up to about 25% by weight of polymer. In still other embodiments of the present invention, the bone graft materials may comprise one or more biocompatible polymers that comprise the above percentages. In some embodiments, the amount of one or more biocompatible polymer ranges from about 15% to about 40%, preferably from about 15% to about 30% relative to the total weight of the dry bone graft material. In a preferred embodiment of the present invention, the bone graft material comprises up to 20% by weight of a first polymer and up to 20% by weight of a second polymer, relative to the total weight of the dry bone graft material. In another preferred embodiment, the bone graft material comprises up to 10% by weight of one polymer and up to 16% by weight of a second polymer, relative to the total weight of the dry bone graft material. In yet another preferred embodiment, the bone graft material comprises from about 5% to 20%, preferably from 5% to about 15% by weight of a first polymer and from about 5% to about 20%, preferably from 10% to about 20% by weight of a second polymer, relative to the total weight of the dry bone graft material.

Bone graft materials of the present invention may comprise up to about 20% by weight of bioactive glass. In certain embodiments, bone graft materials of the present invention may comprise up to about 15% by weight of bioactive glass. In certain other embodiments, bone graft materials of the present invention may comprise up to about 10% by weight of bioactive glass. In other embodiments, bone graft materials of the present invention may comprise up to about 12.5% by weight of bioactive glass. In some embodiments, the bone graft material is provided in a form containing bioactive glass while in alternate embodiments, a dose of bioactive glass is provided to be incorporated into the bone graft prior to or during implantation into the surgical site.

In preferred embodiments, the bone graft materials of the present invention exhibit high degrees of porosity. It is also preferred that the porosity occur in a broad range of effective pore sizes. In this regard, the preferred embodiments of the invention may have macroporosity, mesoporosity, and microporosity. The definition of macroporosity, mesoporosity, and microporosity and how the porosity of the materials is measured is disclosed above.

In one embodiment, the bone graft materials of the present invention has pore volumes of greater than about 30%, preferably from greater than about 50% or greater than about 60% and less than 100%.

In preferred cases, such high pore volumes are attained while also attaining the presence of macro- meso-, and microporosity as well as physical stability of the materials produced. It is believed to be a great advantage to prepare graft materials having macro-, meso-, and microporosity simultaneously with high pore volumes that also retain some compression resistance and flexibility, moldability, or flowability when wetted.

Scanning electron micrographs (SEMs) of certain embodiments of the present invention demonstrate the high porosity of these graft materials (see, for example, FIGS. 5A-5D).

Figure 8:
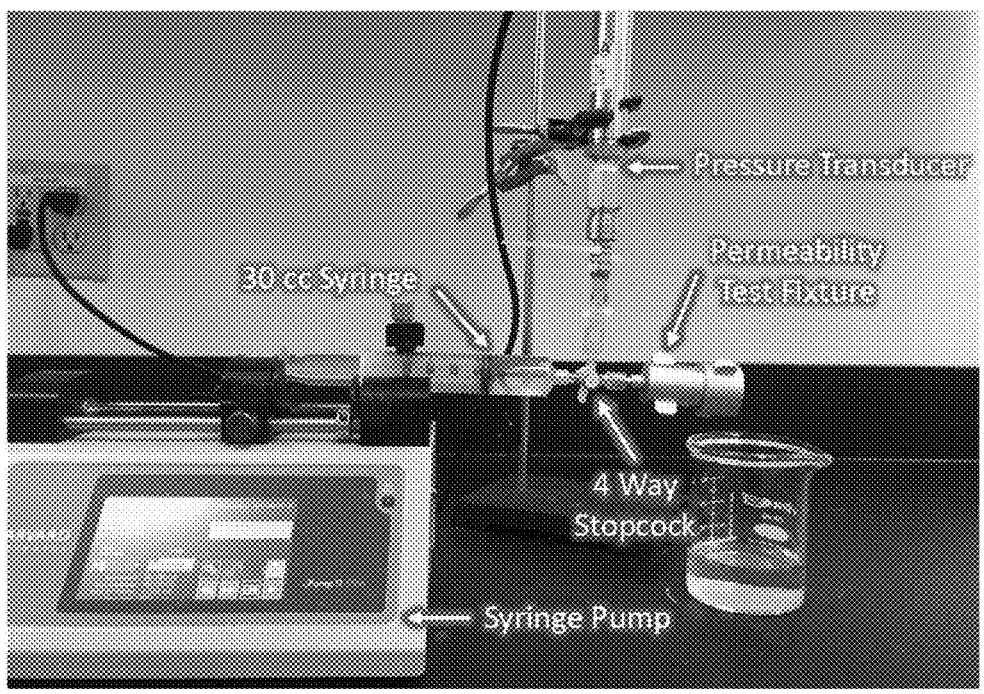
FIG. 8 is a photograph of a test set up used for measuring the water permeability of the flowable bone graft materials.

The flowable bone graft materials of the present invention also exhibit improved wash-out resistant and therefore can maintain physical integrity in a wet environment. Water permeability values correlate to a wash-out resistance of a flowable bone graft material. Water permeability can be measured, for example, using a test set up as illustrated in FIG. 8. The details of the test set up and the test procedure are explained below in Experimental Example 3. Generally, the test set up includes a permeability test fixture which secures the flowable sample to be tested, a pressure transducer and 30 cc syringe. These three components are connected with a 4-way Hi-flow stopcock. A syringe pump (Harvard Apparatus Syringe Pump 11 Elite) is used to deliver a constant fluid flow rate of saline to the permeability test fixture which has the flowable sample while the pressure transducer records pressure due to resistance of the sample. Pressure transducer (Omega USB Pressure Transducer 0-100 PSI) is connected to the stopcock with ¼" ID tygon tubing and luer adapter, and zip ties are used to secure tubing.

The syringe pump is then initiated to begin infusion of the saline into the sample material in the permeability test fixture at 5 ml/min while the pressure transducer records pressure due to resistance of the sample for 1 minute. The material permeability of the flowable bone graft material is calculated according to the following formula:

$$k = \frac{Q\mu L}{AP}$$

wherein Q is the volumetric flow rate (m$^3$/s),
μ is the dynamic viscosity of water (9.4E-4 Pa*s),
L is the thickness of the sample (0.01016 m),
P is the pressure drop across the sample (PA, and
A is the surface area exposed to flow (4.55 E-5 m$^2$).

Water permeability values correlate to a wash-out resistance of a flowable bone graft material. Lower permeability values correlate to a material that is more resistant to wash-out. It is preferred that the flowable bone graft materials of the present invention has water permeability of less than about 1.0E-13 m$^2$, preferably less than about 9.0E-14 m$^2$ when tested in accordance with the procedure described in Experimental Example 3. In another embodiment, water permeability of the flowable bone graft material is from about 1.0E-14 m$^2$ to about 1.0E-13 m$^2$, preferably from about 1.0E-14 m$^2$ to about 9.0E-14 m$^2$, more preferably from about 2.0E-14 m$^2$ to about 6.0E-14 m$^2$, and most preferably from about 3.0E-14 m$^2$ to about 4.4E-14 m$^2$. Water permeability of the flowable bone graft material is tested as described in Experimental Example 3.

Bone graft materials of the present invention have osteoconductive and osteostimulatory properties. In certain embodiments, the addition of bioactive glass in the present invention enhances the ability of the product to foster bone growth. The bone graft materials of the present invention may also have osteoinductive properties.

Kit

Another aspect of the present invention provides a kit comprising a syringe containing a dry bone graft material comprising calcium phosphate having a particle size of about 100 μm to about 1,000 μm, bioactive glass, and one or more biocompatible polymers comprising sodium carboxymethyl cellulose. In a preferred embodiment, the syringe further contains gelatin as an additional biocompatible polymer. In another preferred embodiment, the syringe containing the dry bone graft material does not contain any fluid such as bone marrow aspirate, blood or saline.

Figure 2:
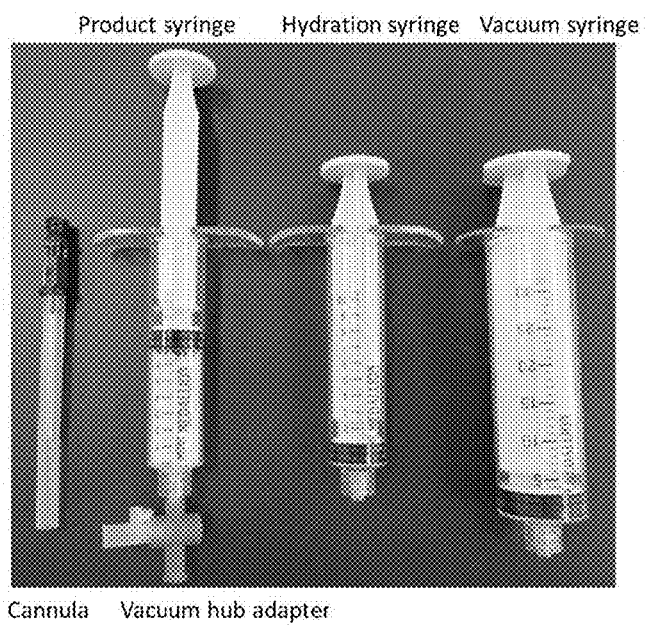
FIG. 2 depicts another embodiment of a kit described herein including a syringe (product syringe) containing the dry bone graft material, a hydration syringe, a vacuum syringe, a vacuum hub adapter and a cannula.
Figure 3:
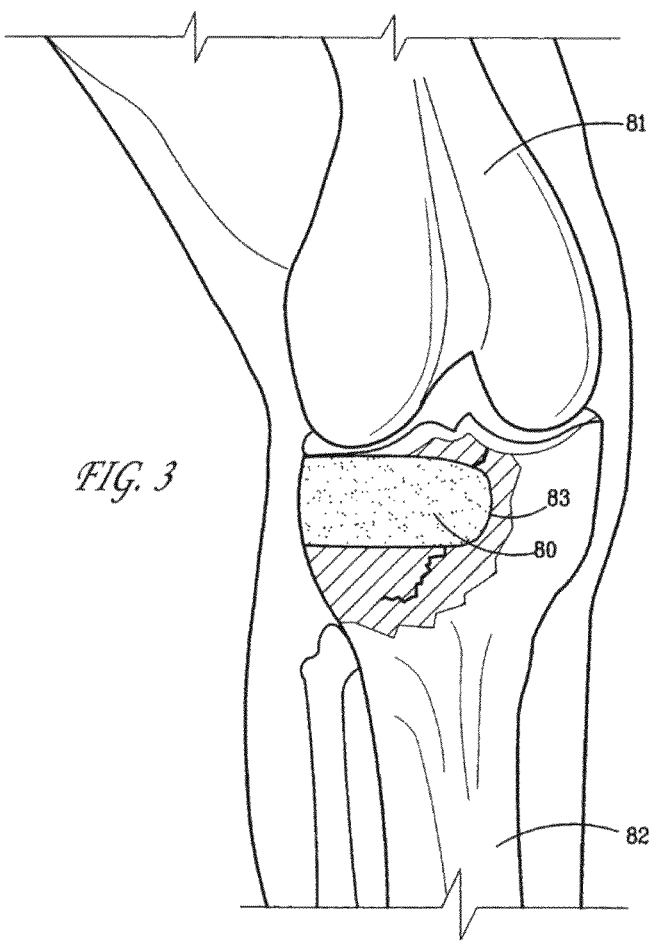
FIG. 3 illustrates the bone graft material 80 injected into a bone void 83 below the femur 81 in the tibial plateau 82 within a human knee.
Figure 4:
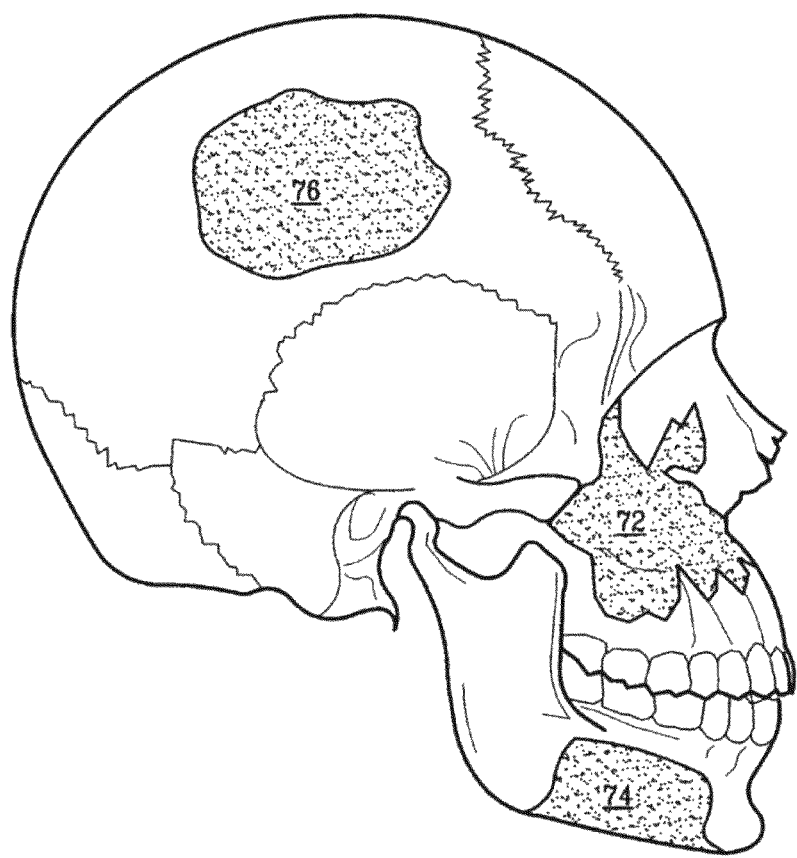
FIG. 4 illustrates the graft material of the present invention injected to serve as a cranio-maxillofacial 76, zygomatic reconstruction 72 and mandibular implant 74.
Figure 5A:
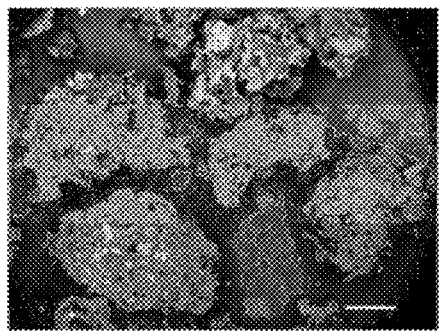
FIGS. 5A, 5B, 5C and 5D are respectively 30×, 100×, 250×, and 100× of Scanning Electron Microscopy (SEM) images of one embodiment of the dry bone graft material of the present invention comprising 62.5% by weight of calcium phosphate, 15% by weight of gelatin, 10% by weight of sodium carboxymethyl cellulose and 12.5% Combeite bioactive glass-ceramic, wherein the bone graft material does not contain any fluid.
Figure 5B:
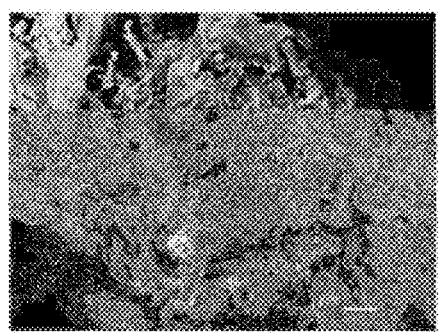
Figure 5C:
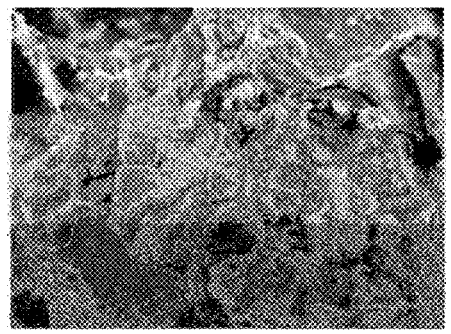
Figure 5D:
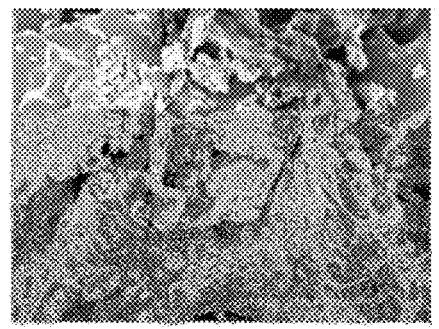

In a preferred embodiment, the kit further comprises a hydration syringe to be filled with a fluid, such as bone marrow aspirate, blood or saline; a vacuum syringe to pull vacuum and expel air in the syringe containing the dry bone graft material; and a cannula for injecting the bone graft material once the dry bone graft material and the fluid are mixed and forms a flowable bone graft material in situ in the syringe. Illustrative components of kits are shown in FIGS. 1 and 2.

In accordance with the present invention, fluids are directly aspirated into or injected into a syringe body containing a dry bone graft material thereby forming a flowable bone graft material "in situ" in the syringe body that is cohesive and injectable.

In another preferred embodiment, a kit comprises a container or a syringe containing a dry bone graft material containing one or more biocompatible polymers and the inorganic composition, without any bioactive glass. In such embodiment, the bioactive glass is provided in a distinct separate container or in a syringe to be combined with the dry bone graft material before use at a later date. The distinct separate container including the bioactive glass may be adapted to connect to the syringe containing the dry bone graft such that homogenous mixing back and forth is permitted. Thus, ultimately, a composite apparatus capable of mixing the components into a substantially homogenous bone graft material containing calcium phosphate, biocompatible polymer, and bioactive glass is provided.

Kits of the present invention provide an easy-to-use dose of flowable bone graft material. After mixing with desired fluids such as blood, bone marrow aspirate, or saline, with the dry bone graft material, the present invention is capable of being delivered via injection through small orifices such as 12-gauge or 10-gauge cannulas or catheters. A variety of other fluids could also be used with the present invention including blood, bone marrow aspirate, saline, antibiotics, proteins such as bone morphogenetic proteins ("BMP"), molecules, vectors, therapeutic agents, and combinations thereof.

Method of Making Flowable Bone Graft Materials

Described herein are methods of making the flowable bone graft materials of the present invention. In one embodiment, a method for preparing a flowable bone graft material comprises dissolving gelatin in a solvent, such as water; adding calcium phosphate mineral particles having a size ranging from about 100 μm to about 1,000 μm, preferably of about 212 μm to about 850 μm; adding bioactive glass particles having a size ranging from about 20 μm to about 200 μm, preferably having a bimodal distribution of particle size having a first set of particles in the size ranging from 32 μm to 90 μm and a second set of particles in the size range about 90 μm to about 150 μm; adding a lower alkyl cellulose ether, preferably sodium carboxymethyl cellulose; lyophilizing the third mixture; morselizing the lyophilized mixture, preferably in a size ranging from 0.5 mm to 2 mm, more preferably from 0.5 mm to 1 mm; and placing the dry bone graft material in a syringe.

In another embodiment, a method for preparing a flowable bone graft material comprises dissolving gelatin in a solvent, such as water, to form a gelatin solution; adding calcium phosphate mineral particles having a size ranging from about 100 μm to about 1,000 μm, preferably of about 212 μm to about 850 μm to the gelatin solution in a specified amount and in specified increments over time to form a first mixture; adding bioactive glass particles having a size ranging from about 20 μm to about 200 μm, preferably having a bimodal distribution of particle size having a first set of particles in the size ranging from about 32 μm to about 90 μm and a second set of particles in the size range about 90 μm to about 150 μm, to the first mixture at room temperature in a specified amount and in specified increments over time to form a second mixture; and adding a lower alkyl cellulose ether, preferably sodium carboxymethyl cellulose, to the second mixture in a specified amount and in specified increments over time to form a third mixture; lyophilizing the third mixture; morselizing the lyophilized third mixture to produce a dry bone graft material, preferably having a size ranging from about 0.5 mm to about 2 mm, more preferably from about 0.5 mm to about 1 mm; and placing the dry bone graft material in a syringe.

In one embodiment, the amount of gelatin added is from about 5% to about 20%, preferably from about 10% to about 20%, and more preferably from about 13% to about 16%, relative to total weight of the dry components of the bone graft material. In one embodiment, the amount of calcium phosphate added is from about 50% to about 70%, and preferably from about 55% to about 65%, relative to total weight of the dry components of the bone graft material. In another embodiment, the amount of bioactive glass added is from about 10% to about 20%, and preferably from about 10% to about 15, relative to total weight of the dry components of the bone graft material. In yet another embodiment, the amount of a lower alkyl cellulose ether added is from about 5% to 20%, and preferably from about 5% to 15%, relative to total weight of the dry components of the bone graft material.

In one embodiment, the gelatin is added to a solvent in 1 to 5 substantially equal increments over time, preferably from 3 to 5 substantially equal increments over time. In another embodiment, the calcium phosphate is added to the gelatin solution in 1 to 5 substantially equal increments over time, preferably from 3 to 5 substantially equal increments over time. In another embodiment, the bioactive glass is added to the first mixture in 1 to 4 substantially equal increments over time, preferably from 2 to 4 substantially equal increments over time. In yet another embodiment, a lower alkyl cellulose ether is added to the second mixture in 1 to 5 substantially equal increments over time, preferably from 3 to 5 substantially equal increments over time.

In yet another embodiment of the present invention, the graft material may be shredded or cut into small pieces. These smaller shredded pieces, preferably in a size range of 0.5 mm to 2 mm, more preferably in a size range of 0.5 mm to 1 mm, could then placed in a syringe body. The shredded pieces allow for high surface area exposure for optimal mixing with fluids to produce a cohesive injectable putty, which finds particular use as filler for irregular bone void defects and can be injected to insure maximum contact with adjacent bone for beneficial healing.

In another preferred embodiment, the biocompatible polymer and the inorganic composition are combined as described, and the bioactive glass is provided as a distinct separate container, to be incorporated into the dry bone graft material, for example, by a surgeon, during preparation for use in the surgical site.

An alternate embodiment of the present invention provides a method for restoring or repairing bone in an animal comprising accessing a site to be restored; loading a product syringe with a dry bone graft material preferably having a size ranging from about 0.5 mm to 2 mm, more preferably from about 0.5 mm to about 1 mm; connecting a vacuum syringe to the product syringe; expelling air and pulling vacuum from the product syringe using the vacuum syringe; disconnecting the vacuum syringe from the product singe; connecting a hydration syringe containing a fluid to the product syringe; mixing the dry bone graft with the fluid using the hydration syringe by passing the material back and forth between the syringes for a total of from about 5 to about 20 passes, preferably from about 10 to about 16 passes, to form a flowable bone graft material in situ, wherein the initial transfer of saline to bone graft material constitutes as one pass, and transferring back constitutes a second pass; disconnecting the syringes; attaching a cannula to the syringe containing the bone graft material, which could be either the product syringe or the hydration syringe; positioning the cannula at the site to be restored; delivering the flowable bone graft at a force of less than 140 N, preferably less than 100 N, more preferably from about 50 N to about 100 N extrusion force.

In accordance with the present invention, fluids are directly aspirated into or injected into a syringe body containing a dry bone graft material thereby forming a flowable bone graft material "in situ" in the syringe body that is homogeneous, cohesive and injectable depending upon the application requirements.

Yet another embodiment of the present invention provides a method for restoring or repairing bone in an animal comprising accessing a site to be restored; loading a product syringe with a dry bone graft material preferably having a size ranging from about 0.5 mm to about 2 mm, more preferably from about 0.5 mm to about 1 mm; filling a hydration syringe with a desired fluid; providing a vacuum syringe to pull vacuum and expel air in the product syringe containing the dry bone graft material; mating the product syringe, the hydration syringe, and the vacuum syringe to three respective luers on a vacuum hub adapter; using the vacuum syringe to pull vacuum and expel air; removing the vacuum syringe from the luer; mixing the dry bone graft with the fluid using the hydration syringe to form a flowable bone graft material in situ in the product syringe; removing the product syringe from the vacuum hub adapter; attaching a 10-gauge cannula to the product syringe; positioning the cannula at the site to be restored; delivering the flowable bone graft to the site to be restored at a force of less than 140 N, preferably less than 100 N, more preferably from about 50 N to about 100 N extrusion force.

Methods of Repairing Bone

In one embodiment, the present invention provides a method in which fluid mixes with bone graft material to provide a flowable homogeneous mass that can be injected into the site without requiring the user to touch or knead the material. In one embodiment, the flowable bone graft material is to be used in MIS (minimally invasive spine surgery) procedures.

In one embodiment, the method for repairing bone in an animal comprises forming a flowable bone graft material comprising an inorganic composition comprising calcium phosphate having a particle size of about 100 µm to about 1,000 µm, bioactive glass, one or more biocompatible polymers comprising sodium carboxymethyl cellulose, and a fluid; accessing a site to be restored; and delivering the bone graft material to the site.

Many of the embodiments disclosed herein are to fill bony voids and defects. It will be appreciated that applications for the embodiments of the present invention include, but are not limited to, filling interbody fusion devices/cages (ring cages, cylindrical cages), placement adjacent to cages (i.e., in front cages), placement in the posterolateral gutters in posterolateral fusion (PLF) procedures, backfilling the iliac crest, acetabular reconstruction and revision hips and knees, large tumor voids, use in high tibial osteotomy, burr hole filling, and use in other cranial defects. The bone graft material strips may be suited for use in PLF by placement in the posterolateral gutters, and in onlay fusion grafting. Additional uses may include craniofacial and trauma procedures that require covering or wrapping of the injured/void site. The bone graft material cylinders may be suited to fill spinal cages and large bone voids, and for placement along the posterolateral gutters in the spine.

It should be understood that the present invention graft material could be used in a wide variety of applications such as in numerous bone void filling applications and filling of interbody fusion devices. In applications requiring graft materials with load bearing capabilities, the graft materials of the present invention may be used in conjunction with standard orthopedic hardware including meshes, plates, screws, rods, sutures, staples, cerclage wire, implants of metal, such as titanium or stainless steel, or of a polymer or composite polymer such as polyetheretherketone ("PEEK"), or nitinol.

The present invention may also be used in conjunction with orthopedic load-bearing materials such as vertebral body replacement devices and spinal implants, such that the present invention material is injected in the openings of such devices. The load-bearing frame may be made of a metal such as titanium or of a load-bearing resorbable composite such as PEEK or a composite of some form of poly-lactic acid ("PLA"). In the case of the latter, the acid from the PLA co-acts, or interacts with the calcium phosphate of the embedded bone graft material to provide an implant with superior resorption features.

EXAMPLES

Example 1: Manufacture of Dry Bone Graft Material

Porous calcium phosphate was prepared, and then was crushed and sieved to obtain morsels in the size range of 212 μm to about 850 μm.

Gelatin (Gelita 250 Bloom MedellaPro Type A NF pork skin) was dissolved in water at room temperature. The gelatin solution was refrigerated overnight at 2° C. to 8° C. The refrigerated gelatin was warmed in a warming chamber at 50° C. so that the center of the gelatin was from about 18° C. to 20° C., and the periphery of the container was from about 24° C. to 25° C. The warmed gelatin was cut into four roughly equal sized pieces and the gelatin was mixed for about 10 minutes. Next, calcium phosphate mineral particles having a size range of about 212 μm to about 850 μm was added to the gelatin at room temperature in five roughly equal increments. Next, nonporous Combeite was added in four roughly equal increments. The particle size of Combeit had a bimodal particle size distribution of 32 μm-90 μm and 90 μm-150 μm. Next, sodium carboxymethyl cellulose (Ashland: Aqualon CMC 7M8SF PH/Product No. 414263) was added in four roughly equal increments. The amounts of gelatin, calcium phosphate particles, Combeite, and sodium carboxymethyl celluloses added are listed in Table 1 below. The sodium carboxymethyl cellulose component of EXAMPLE 1 had a viscosity of 400-800 MPa-s, 0.7 degree of substitution and MW of 250,000.

TABLE 1

| Component | Dry Mass (g) | Amount (wt %) based on dry fill weight |
|---|---|---|
| Gelatin | 144 | 15 |
| Calcium phosphate | 600 | 62.5 |
| Nonporous Combeite | 120 | 12.5 |
| Sodium carboxymethyl cellulose | 96 | 10 |

The mixture was then placed onto trays and lyophilized. Subsequently, the lyophilized material was then morselized in a size range of 0.5 mm to 2 mm to produce resultant dry bone graft material.

Example 2-4: Manufacture of Flowable Bone Graft Material

The morselized dry bone graft material from Example 1 was placed in a product syringe. Then the product syringe was connected to a vacuum syringe to expel out of the product syringe. After disconnecting the vacuum syringe from the product singe, a hydration syringe containing saline was connected to the product syringe. The plunger of the product syringe was depressed as the saline in the hydration was passed into the product syringe. There was a 5 second waiting period before it was further mixed by passing the material back to another syringe. The material was transferred back and forth between the product syringe and hydration syringe till it was properly mixed. The initial transfer of saline in the hydration syringe to dry bone graft material in the product syringe constituted as one pass and transferring back constitutes a second pass and so on. Each pass included 5 second waiting time before the material was transferred to another syringe.

Various formulations were made, for example, using different amounts of saline and different amounts of passes, and whether a vacuum syringe to pull the vacuum of the product syringe is used or not as shown in Table 2 below:

TABLE 2

| Formulation | Amounts of Saline | Number of Passes for mixing | Amount Of dry bone graft material | Vacuum pulled |
|---|---|---|---|---|
| Example 2 | 2.2 cc | 15 | 1.2 g | yes |
| Example 3 | 3 cc | 15 | 1.2 g | yes |
| Example 4 | 2.2 cc | 1 | 1.2 g | yes |
| Example 5 | 2.2 cc | 15 | 1.2 g | no |

Comparative Example 1

Dry bone graft material was prepared in the same manner as in Example 1, except that sodium carboxymethyl cellulose was not added. The amounts of the ingredients in this Comparative Example is provided below in Table 3:

TABLE 3

| Component | Dry Mass (g) | Amount (wt %) |
|---|---|---|
| Gelatin | 144 | 22.5 |
| Calcium phosphate | 400 | 62.5 |
| Combeite | 96 | 15 |

Comparative Example 2

A commercially available product, VITOSS FOAM FLOW (Stryker Orthobiologics) was tested. This product contains collagen as the biocompatible polymer and does not contain sodium carboxymethyl cellulose or gelatin. This product also does not contain bioactive glass.

Examples 6-11

Flowable bone graft material was prepared in the same manner as in Example 2, except sodium carboxymethyl cellulose used had the following viscosities, degrees of substitution and amounts of as provided below in Table 4:

TABLE 4

| Formulation | Viscosity (MPA-s) | Degrees of Substitution | Amount (wt %) based on dry fill weight |
|---|---|---|---|
| Example 2 | 400-800 | 0.7 | 10 |
| Example 6 | 300-800 | 0.9 | 10 |
| Example 7 | 300-800 | 0.9 | 7.5 |
| Example 8 | 300-800 | 0.9 | 5 |
| Example 9 | 400-800 | 0.7 | 9.1 |

TABLE 4-continued

| Formulation | Viscosity (MPA-s) | Degrees of Substitution | Amount (wt %) based on dry fill weight |
|---|---|---|---|
| Example 10 | 400-800 | 0.7 | 8.5 |
| Example 11 | 400-800 | 0.7 | 8.1 |

Experimental Example 1: Scanning Electron Microscopy Evaluation

Scanning electron micrographs (SEM) of one embodiment of the dry bone graft material of Example 1 are provided in FIGS. 5A-5D. It was confirmed that the dry bone graft material had a substantially homogeneous mixture of calcium phosphate, biocompatible polymers, and bioactive glass throughout the dry bone graft material.

Experimental Example 2: Mixing Test

The evaluations of mixing properties of various formulations are summarized below in Table 5.

TABLE 5

| Formulations | Extrusion Test Results |
|---|---|
| Example 2 | Mixed well; smooth, material provides little resistance and passes fully between syringes on first pass. |
| Example 6 | Could not be mixed; material requires unusual force such as the use of the countertop; material requires 11-15 transfers to completely transfer material between syringes; and/or a non-hydrated puck of greater than 0.2 cc remains in the syringe and does not mix |
| Example 7 | Mixed well; smooth, material provides little resistance and passes fully between syringes on first pass. |
| Example 8 | Mixed well; smooth, material provides little resistance and passes fully between syringes on first pass. |
| Example 9 | Mixed well; smooth, material provides little resistance and passes fully between syringes on first pass. |
| Example 10 | Mixed well; smooth, material provides little resistance and passes fully between syringes on first pass. |
| Example 11 | Mixed well; smooth, material provides little resistance and passes fully between syringes onfirst pass. |

Figure 7:
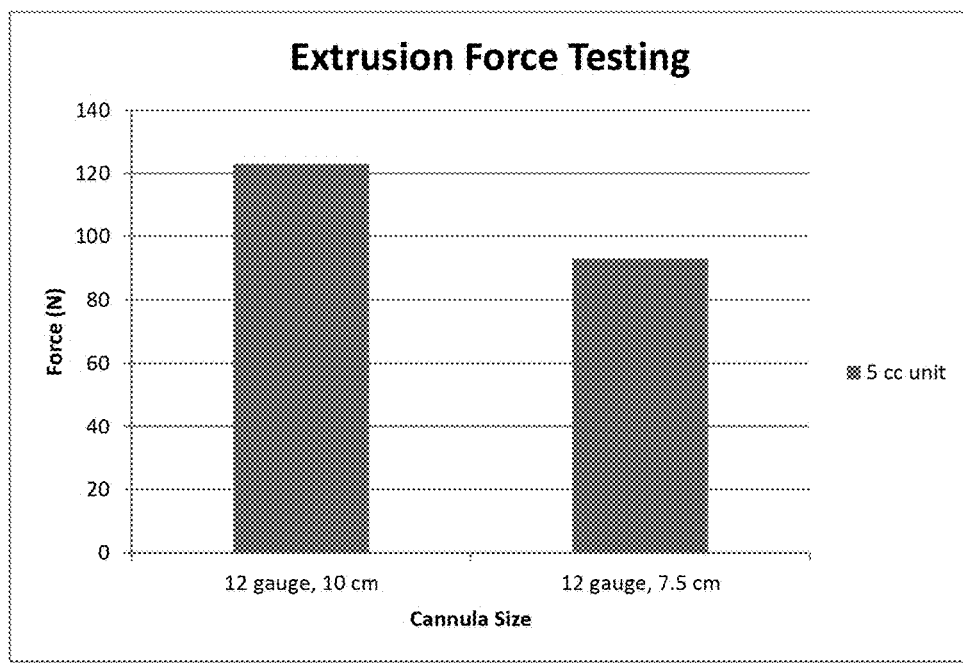
FIG. 7 summarizes the results of extrusion force test of the bone graft materials.

Experimental Example 3: Extrusion Force 5 cc of saline was directly injected into a syringe body containing a 2.4 g dry bone graft material and mixed for 15 passes and thereby forming a flowable bone graft material "in situ". Extrusion force was tested using 12-guage cannula having two different lengths, 5 cm and 10 cm, respectively at a rate of 0.25 cc/sec. The results of the extrusion force testing using the bone graft material of Example 1 is provide in FIG. 7. As illustrated, the extrusion force required to extrude the flowable bone graft material through a 12 gauge did not exceed 140 N.

The results of extrusion tests of various other formulations are summarized below in Table 6:

TABLE 6

| Formulations | Extrusion Test Results |
|---|---|
| Example 2 | Extrusion material is easy requiring little force and is easy to control volume. |
| Example 6 | n/a (could not be mixed and therefore could not be tested for extrusion) |
| Example 7 | Material has intermittent clogs but volume dispensed can be controlled and/or material requires intermediate amounts of force to extrude (requiring some strain on the thumb to depress syringe plunger). |
| Example 8 | Extrusion material is easy requiring little force and is easy to control volume. |
| Example 9 | Extrusion material is easy requiring little force and is easy to control volume. |
| Example 10 | Extrusion material is easy requiring little force and is easy to control volume. |
| Example 11 | Extrusion material is easy requiring little force and is easy to control volume. |

Experimental Example 3: Water Permeability Tests/Wash-Out Resistant Properties

Water permeability testing was performed to determine wash-out resistant properties on various formulations. As shown in FIG. 8, the test set up included a permeability test fixture which secured the flowable sample to be tested, a pressure transducer and 30 cc syringe. These three components were connected with a 4-way Hi-flow stopcock. A syringe pump (Harvard Apparatus Syringe Pump 11 Elite) was used to deliver a constant fluid flow rate of saline to the permeability test fixture which had the flowable sample while the pressure transducer recorded pressure due to resistance of the sample. Pressure transducer (Omega USB Pressure Transducer 0-100 PSI) was connected to the stopcock with ¼" ID tygon tubing and luer adapter, and zip ties are used to secure tubing.

Figure 9:
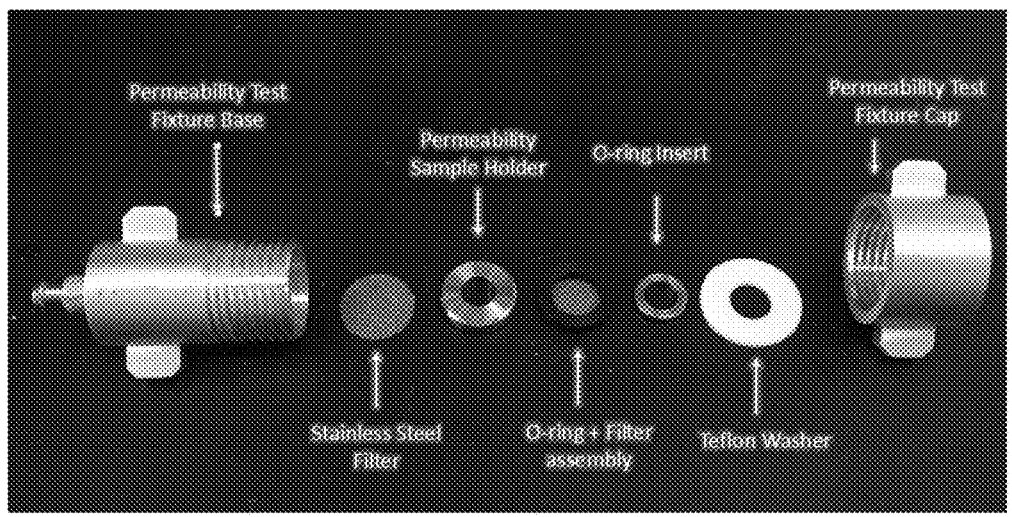
FIG. 9 is a photograph of the components of a permeability test fixture used in the test set up to measure water permeability.
Figure 10:
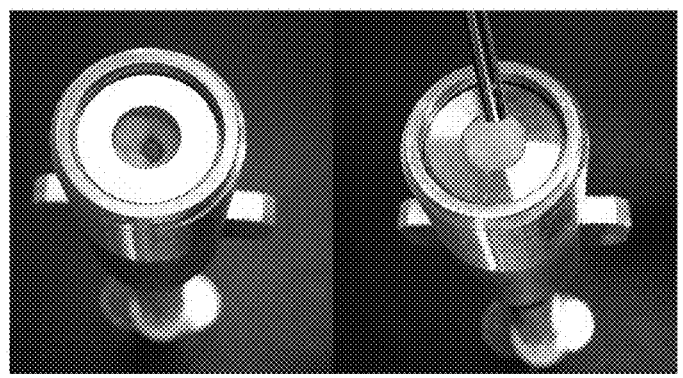
FIG. 10 is a picture of a sample holder in the permeability test fixture and the flowable bone graft material therein.

One of the components of the test set up, i.e., the permeability test fixture, was prepared by assembling the components shown in FIG. 9 from left to right. The components included a fixture base, ¾" OD stainless steel filter, a sample holder, O-ring+½" OD stainless steel filter assembly, O-ring insert, Teflon washer and a fixture cap. First, one ¾" OD stainless steel filter was placed flush in the test fixture base. Then 6 cc syringe was filled with 3.00 cc sterile saline and was connected to the test fixture base luer connector. The test fixture base was filled up with saline up to the steel filter. Then, as shown in FIG. 10, the prepared flowable bone graft material was extruded into the sample holder by first filling the material in the perimeter and then filling from the bottom up to ensure no air pockets are trapped within the sample. Subsequently, the second O-ring+½" OD stainless steel filter assembly was assembled on top of the sample holder. Then the O-ring insert was pressed into the O-ring so that the O-ring sealed around the perimeter of the base and protruded from the test fixture base. Lastly, the permeability test fixture cap was screwed onto the base. Then, the 6 cc syringe was removed from the permeability test fixture base, and the base was connected to the 4 way stopcock of the test set up.

The syringe pump was initiated to begin infusion of the saline into the sample material in the permeability test fixture at 5 ml/min while the pressure transducer recorded pressure due to resistance of the sample for 1 minute.

Figure 6:
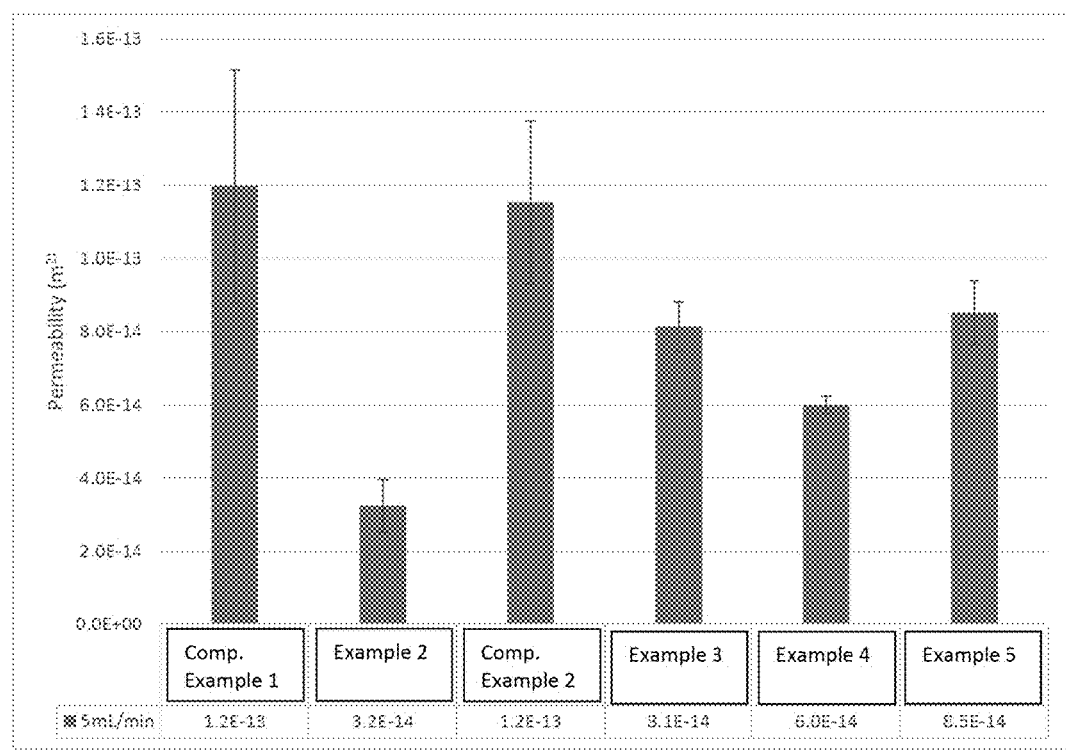
FIG. 6 is a graph showing the results of water permeability testing of various bone graft materials in accordance with the present invention (EXAMPLES 2-5) and Comparative Examples.

Water permeability testing was performed on Example 2 containing 62.5% β-TCP; 12.5% BA glass; 15% gelatin and 10% sodium carboxymethyl cellulose by weight of the dry bone graft material, wherein the sodium carboxymethyl cellulose component of EXAMPLE 2 had a viscosity of 400-800 MPa-s, and 0.7 degree of substitution. Lower permeability values correlate to a material that is more resistant to wash-out. The results of the water permeability testing of Examples 2-5 and Comparative Example Examples 1-2 are provided in FIG. 6. Example 2 showed lowest permeability value, which correlates to the highest wash-out resistance. Moreover, Examples 2-5 showed lower permeability value (which correlates to higher wash-out resistance) compared to Comparative Examples 1 and 2.

Experimental Example 4: Injection in Fluid

Materials of different formulations were prepared and injected into a 600 mL beaker containing 400 mL of PBS. If the material remained cohesive and did not disintegrate when injected in the fluid, then the formulation passed the injection test. The results of the tests of various other formulations are summarized below in Table 7:

TABLE 7

| Formulations | Injection in fluid |
|---|---|
| Example 2 | Pass |
| Example 9 | Pass |
| Example 10 | Pass |
| Example 11 | Pass |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A flowable bone graft material comprising:
a porous inorganic composition comprising calcium phosphate having a particle size of about 100 μm to about 1,000 μm;
bioactive glass;
one or more biocompatible polymers comprising carboxymethyl cellulose and gelatin; and
a fluid, wherein said fluid is selected from the group consisting of saline, bone marrow aspirate, blood and a mixture thereof
wherein degree of substitution of said carboxymethyl cellulose is from about 0.6 to about 0.8,
wherein said one or more biocompatible polymers does not contain collagen,
wherein molecular weight of said carboxymethyl cellulose is from about 100,000 MW to about 300,000 MW, and
wherein said carboxymethyl cellulose is present in an amount of about 5% to about 15% by weight of said bone graft material.

2. The bone graft material of claim 1, wherein said carboxymethyl cellulose is sodium carboxymethyl cellulose.

3. The bone graft material of claim 1, wherein viscosity of said carboxymethyl cellulose is from about 400 MPa-s to about 800 MPa-s.

4. The bone graft material of claim 1, wherein said gelatin is present in an amount of about 10% to about 20% by weight of said bone graft material excluding the fluid.

5. The bone graft material of claim 1, wherein said one or more biocompatible polymers are present in an amount of about 15% to about 40% by weight of said bone graft material excluding the fluid.

6. The bone graft material of claim 1, wherein said calcium phosphate is present in an amount from about 50% to about 70% by weight of said bone graft material excluding the fluid.

7. The bone graft material of claim 1, wherein said bioactive glass is present in an amount of about 10% to about 20% by weight of said bone graft material excluding the fluid.

8. The bone graft material of claim 1, wherein said inorganic composition comprises beta-tricalcium phosphate.

9. The bone graft material of claim 1, wherein the bioactive glass is 45S5 or combeite glass-ceramic.

10. The bone graft material of claim 1, further comprises an antibiotic, a bone morphogenic protein, or a therapeutic agent.

11. The bone graft material of claim 1, wherein said bone graft material is capable of being delivered via injection through a 12-gauge cannula or catheter.

12. The bone graft material of claim 1, wherein the amount of force required to extrude 5 cc of the bone graft material through a 12-guage cannula of 7.5 cm in length at a rate of 0.25 cc/sec is less than 100 N.

* * * * *